(12) United States Patent
Lienard et al.

(10) Patent No.: US 6,976,785 B2
(45) Date of Patent: Dec. 20, 2005

(54) METHOD AND DEVICE FOR CALIBRATING A RADIOLOGICAL IMAGE

(75) Inventors: Jean Lienard, Igny (FR); Francisco Sureda, Chatenay Malabry (FR); Regis Vaillant, Villebon sur Yvette (FR)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 738 days.

(21) Appl. No.: 10/172,286

(22) Filed: Jun. 14, 2002

(65) Prior Publication Data

US 2003/0007603 A1 Jan. 9, 2003

(30) Foreign Application Priority Data

Jun. 18, 2001 (FR) .............................................. 01 07938

(51) Int. Cl.⁷ .............................................. G01D 18/00
(52) U.S. Cl. ..................................................... 378/207
(58) Field of Search .............................. 378/4, 21, 207, 378/901; 382/131, 132

(56) References Cited

FOREIGN PATENT DOCUMENTS

| EP | 0374045 | | 6/1990 | |
|---|---|---|---|---|
| FR | 2631810 | | 12/1989 | |
| FR | 2803507 | | 7/2001 | |
| JP | 02298845 A | * | 12/1990 | .......... G01N/23/18 |
| JP | 05099643 A | * | 4/1993 | .......... G01B/15/00 |
| JP | 09068418 A | * | 3/1997 | .......... G01B/15/00 |

* cited by examiner

*Primary Examiner*—Edward J. Glick
*Assistant Examiner*—Chih-Cheng Glen Kao
(74) *Attorney, Agent, or Firm*—Jay L. Chaskin; Cantor Colburn LLP

(57) ABSTRACT

A method and device for calibrating images acquired by radiography comprising an X-ray source, an image acquisition, a support placed between the source and the image acquisition, on which support an object to be X-rayed is intended to be positioned. A region of interest, in which the object is likely to be found, is determined between the support and the image acquisition, the center of gravity of this region is determined and at least one calibration factor of the image or images is determined as a function of the position thus determined.

17 Claims, 3 Drawing Sheets

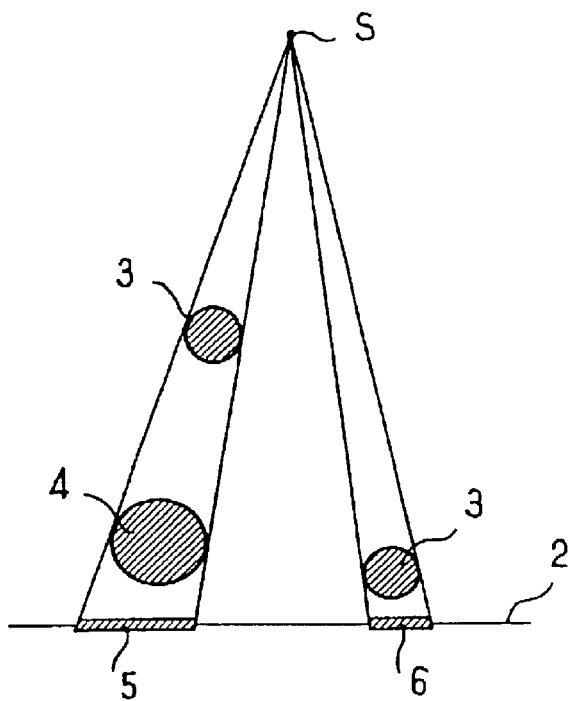
FIG_1
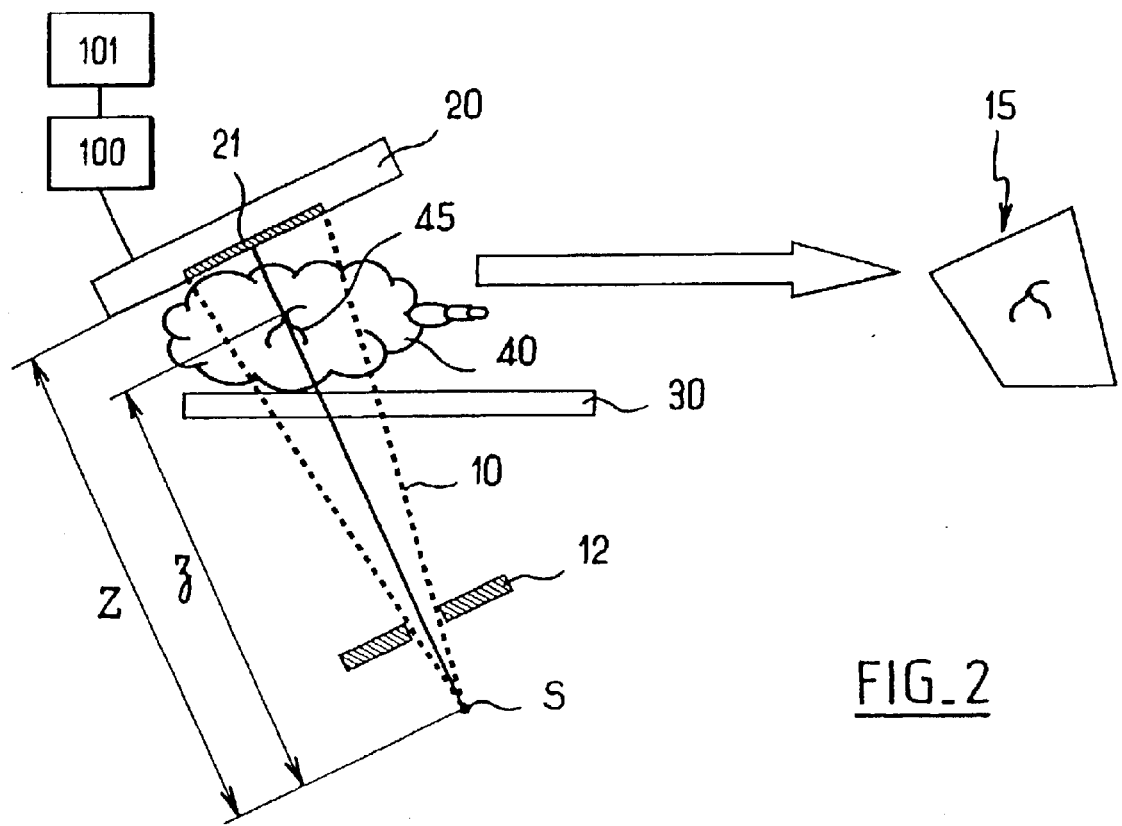
FIG_2

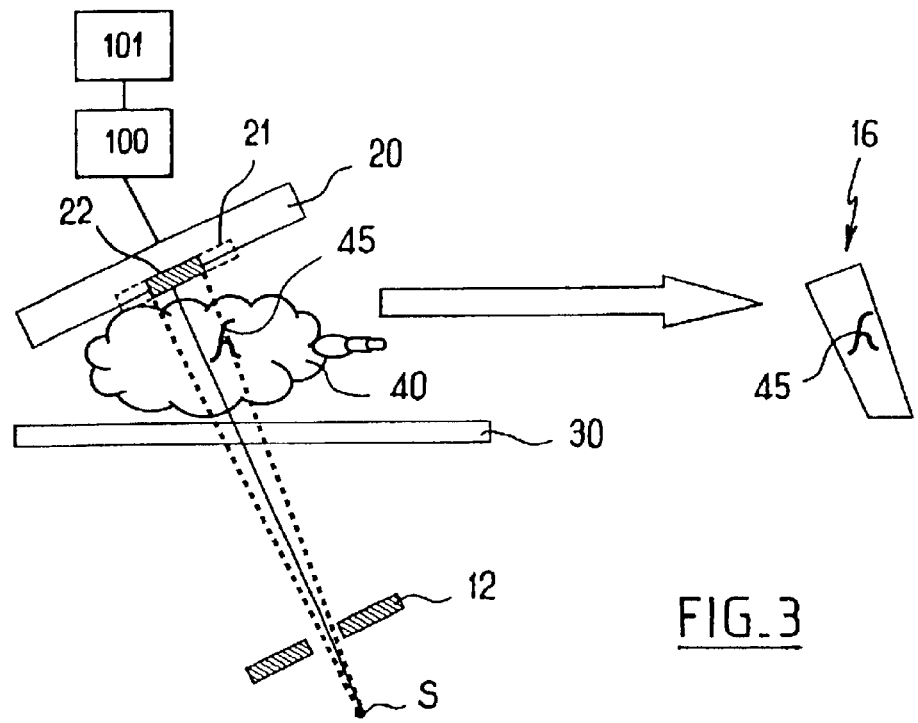
FIG_3
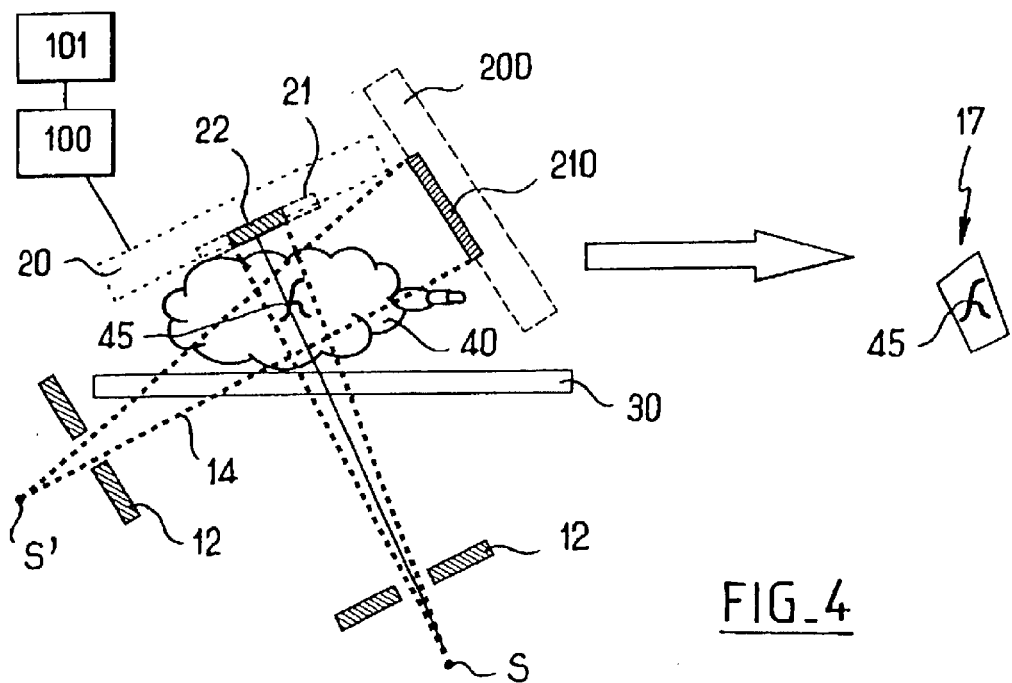
FIG_4

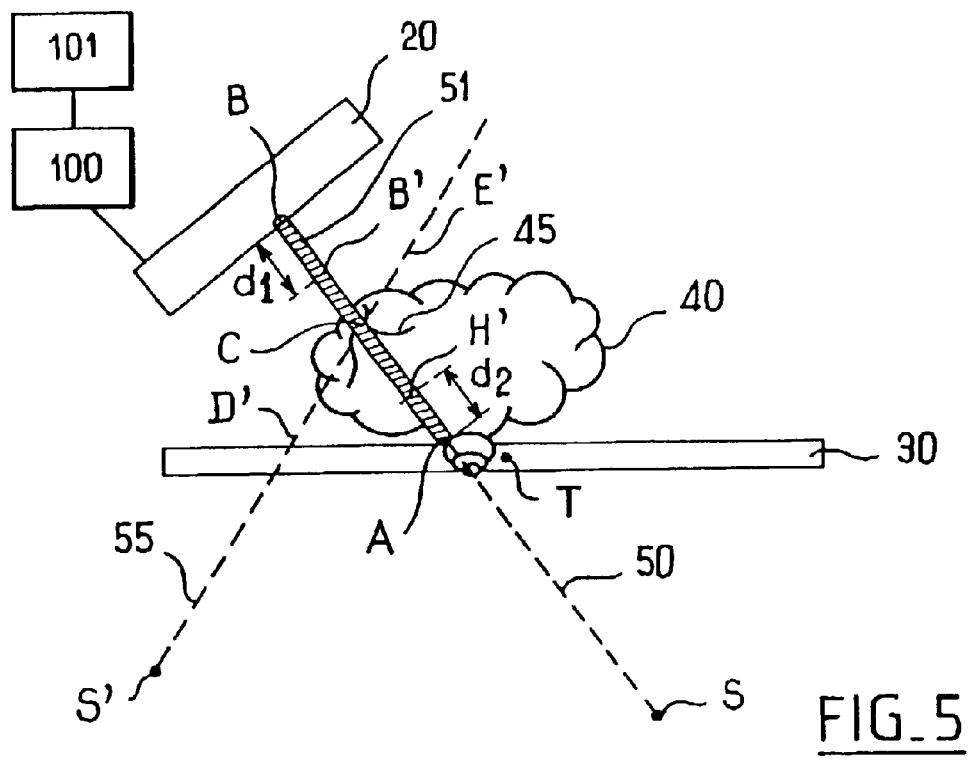
FIG_5
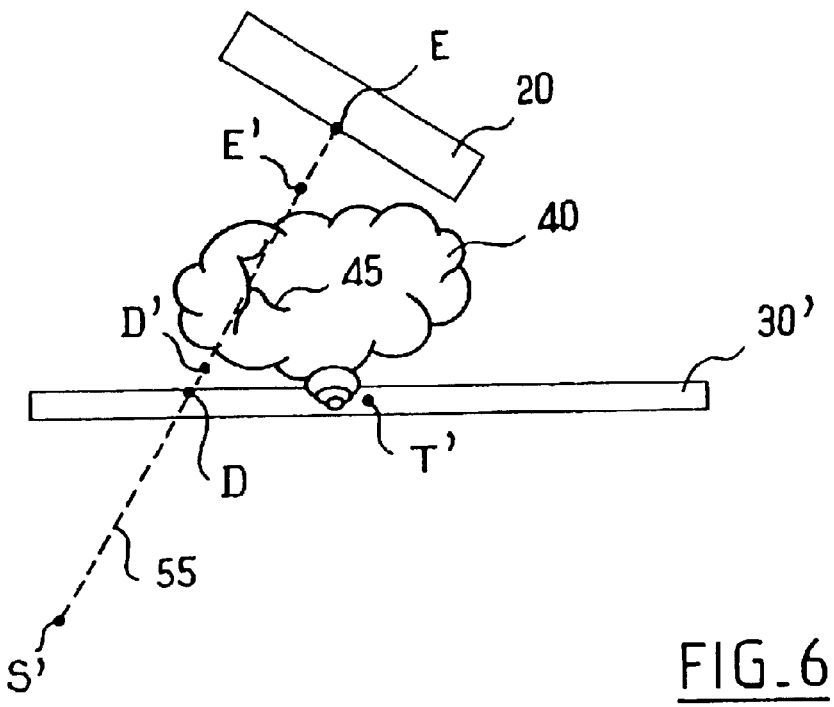
FIG_6

METHOD AND DEVICE FOR CALIBRATING A RADIOLOGICAL IMAGE

CROSS REFERENCE TO RELATION APPLICATIONS

This application claims the benefit of a priority under 35 USC 119 to French Patent Application No. 01 07938, filed Jun. 18, 2001 the entire contents of which are hereby incorporated.

BACKGROUND OF THE INVENTION

This invention relates to a method and apparatus for calibrating a radiological image, and in particular an image by an X-ray radiography device.

The images obtained in X-ray radiography are projections on a plane of two-dimensions (the plane of the means for acquiring an image) of three-dimensional volumes. Due to the loss of one dimension, it is not possible to carry out direct measurements on the images acquired if no calibration procedure is provided. FIG. 1 shows schematically an X-ray source S and a projection plane 2. In this figure, the same object 3 will correspond to projections 5 and 6, on the plane 2, of different sizes, depending on its position between the X-ray source S and the projection plane 2. Similarly, two objects 3 and 4 of different sizes may correspond to the same projection 5 on the plane 2. A calibration procedure enables calculating the sizes of elements appearing on the acquired images. Generally, the calibration procedure comprises identifying an object whose dimensions are known, located in the immediate proximity of the region to be measured. Such an object may be a catheter, a sphere or even a grid. Knowing the dimensions of this object, it is possible to determine the dimensions of the elements which appear on the acquired images and which are substantially in the same plane as the object which is acting as a standard. However, this calibration procedure is relatively tedious since each time requires: positioning a standard object, the dimensions of which are known, in a suitable place; acquiring the dimensions of the standard object at the X-ray device; and if necessary, take acquired X-ray images of the object.

This known procedure penalizes the productivity and is, furthermore, harmful to the patient, since the patient will be subject to several X-ray doses for the calibration which will not be directly used in establishing a diagnosis.

BRIEF DESCRIPTION OF THE INVENTION

The invention is a method and apparatus for calibration which substantially avoids these disadvantages. The invention is a method and apparatus for calibration in which the steps which must be implemented are limited and in which the radiation to which the patient is subjected during the calibration is reduced to a strict minimum.

In particular, the invention is a method and apparatus for calibrating an image acquired by a radiography device of the type comprising means for providing a radiation, means for acquiring the image placed, and means for support placed between the source and the means for acquiring an image, on which support an object to be imaged is positioned, where a region of interest, in which the object is likely to be found, is determined between the means for support and the means for acquiring an image, determining the center of gravity of this region and at least one calibration factor of the image or images is determined as a function of the position thus determined.

BRIEF DESCRIPTION OF THE DRAWING

The invention will be better understood from the following description and appended drawings, in which:

FIG. 1 is a schematic view of a radiography configuration;

FIG. 2 is a schematic view of the general definition of the volume of interest;

FIG. 3 is a schematic view of the refinement of the definition of the volume of interest of FIG. 2;

FIG. 4 is a schematic view of the definition of the volume of interest in the case of several X-ray images;

FIG. 5 is a schematic view of the determination of the calibration of an image where the volume of interest is reduced to a segment of interest; and FIG. 6 is a schematic view of the determination of the calibration of an image where the volume of interest is reduced to a segment of interest according to FIG. 5, the device being in a configuration for acquiring an additional image.

DETAILED DESCRIPTION OF THE INVENTION

A X-ray radiography device shown in FIGS. 2 to 5 comprises means for providing a source of radiation, such as an X-ray source S, means 20 for acquiring an image and means for support 30 intended to receive an object 40, a portion (referenced by 45) which is to be imaged.

The source S is capable of emitting, through an orifice of a collimator 12, an X-ray beam 10 directed towards the means 20 for acquiring an image. The means for support 30 positions the object 45 to be X-rayed in the field of the X-ray beam emitted from the source S through the collimator 12, between the source S and the means for acquiring an image 20. The object 40 is, for example, the body of a patient, the object 45 being a blood vessel on which it is desired to determines a diagnosis using one or more X-ray images.

The means for acquiring an image 20 are preferably of the digital type. In addition, the radiography device comprises means for processing 100, which receive the images acquired by the means 20 for acquiring an image and means for interface 101 (screen, keyboard, stylus, etc.) enabling the user to enter into dialogue with the means for processing, and especially to select, on the images, points or regions whose size it is desired to be known.

FIGS. 2 and 3 shows an embodiment of the invention. On acquiring an X-ray image 21, the device, became of its construction, the relative positions of the source S, of the means 20 for acquiring an image and of the support 30 are known. The operator defines, on the image 21, that is presented on the screen of the means 101 for interface, a region or area 22 in which the projection of the object 45 is found. Once this region 22 is defined, the means for processing 100 converts this region 22 into a volume 15, 16, for which it determines the position of the center of gravity. The position of this center of gravity gives an estimate of the distance z between the source S and the object 45 that is to be X-rayed. This estimate is used by the means for processing 100 in order to calibrate the images that will be made of the object 45 and particularly to calculate the magnification factor f between the object 45 and the images. The magnification factor f is equal to the ratio Z/z, where Z is the distance between the source S and the means for acquiring an image 20.

The region defined on the image 21 may be considered, by default, as corresponding to the total area of the image. This consideration avoids the defining operation and even the acquisition of a first image intended for the calibration. However, this assumes that the object 45 is located at the center of this image. If this is not the case, the calculation of the magnification factor is not reliable. Moreover, as illustrated in FIG. 3, the smaller the area 22 defined by the operator on the image, the more accurately the magnification factor f is determined.

It will be noted that for the area 22 to be defined automatically by the means for processing 100, the user has only to point to the object that is to be imaged by X-ray. To this end, the means for processing implements techniques conventionally known per say for outlining an object. Moreover, in some cases, the organ 45 of the patient 40 cannot be perfectly diagnosed on the basis of a single X-ray image. The operator then has to take additional X-ray images 210 of the organ 45. Each of these additional images 210 has corresponding distinct relative positions of the X-ray source S, of the moans for acquisition 20 and of the means for support 30.

The method comprises for each of the additional images 210 obtained, applying a calibration of the type presented above, that is to say in determining, for each image, the position of the center of gravity of a volume of interest between the plane of the means 20 for acquisition and the means for support 30.

An alternative comprises calculating a single estimate of the position of the object 45 for all the image acquisitions. For example, on acquiring a second image, as illustrated in FIG. 4, the X-ray source is located at S' and the means for acquisition at 200. The area of the image 210 defines a beam 14 coming from the X-ray source at S' and of cross section at the means for acquiring an image equivalent to the total area of the image 210. The intersection between beam 14 and the volume of interest 16, defined above for the first images, defines an intersection volume 17, at the center of gravity of which the X-rayed object 45 is assumed to be located. The means for processing 100 determines the position of the center of gravity of the new volume 17 and calculates the respective magnification factors of the projections of the objects 45 in the images 21 and 210. Given that the intersection volume 17 is smaller than the volume of interest of the first picture, the accuracy of the calibration is increased.

If several additional images are available, the intersection volume is the result of the intersection of all the beams 14 with the volume of interest 16 of the first image. However, if one of the beams 14 has no common intersection with the other beams and/or the volume of interest 16, this beam, together with the associated additional image 210, is not taken into account when calculating the calibration, since it involves another region of the object 40 which is being X-rayed.

FIGS. 5 and 6 illustrate another embodiment of the invention. In some cases (such as angiography), it is difficult to determine an area 22 on the image 21, this area is so small that it can be likened to a point B. On the basis of point B, the means for processing defines a segment 50, the other end of which is the X-ray source S. The segment 50 comprises a point C of the object 45. The point B is a projection of the point C on the means for acquisition. Since the segment 50 intersects the support 30 at A, the means for processing defines a segment of interest 51 (indicated as AB) comprising the point C. The means for processing 100 determines the position of the point C of the object 45 as the center of gravity of the segment of interest 51. The position of the center of gravity C gives an estimate of the distance SC between the source S and the object 45. The means for processing uses this estimate to calibrate the images taken and calculates, for this purpose, the magnification factor:

$$f = \frac{SB}{SC}$$

with an accuracy of $$\pm \frac{AB}{2}$$

over the distance SC. However, the object 45 cannot be in direct contact with the means for support 30, that is to say that the object 45 cannot be located at the point A. The means for processing 100 may then displace the point A to a point H' located at a distance $d_2$ from A along the segment SB in the direction of the point B. The point C is then the center of gravity of the segment of interest A'B. The accuracy in the calculation of f then becomes $$\pm \frac{A'B}{2}$$

over the segment SC. Similarly, the object 45 is not in direct contact with the means for acquisition 20, that is to say that the object 45 cannot be at the point B. The means for processing may than displace the point B to a point B' located at a distance $d_1$ from B along the segment SB in the direction of the point S. The point C is then the center of gravity of a new segment of interest A'B'. The accuracy in the calculation of f then becomes $$\pm \frac{A'B'}{2}$$

over the segment SC.

For additional images as above, it is possible to use a calibration method of the type which has just been described, that is to say to determine, for each of the additional images, the position of the center of gravity of a segment of interest between the plane of the means for acquisition 20 and the means for support 30.

An alternative embodiment is to calculate a single estimate of the position of the object 45 for all the additional images. For each of the additional images, the means for processing determines, in a way similar to the segment A'B', an additional segment of interest D'E' over a segment 55, the first end of which is the X-ray source positioned at S' and the second end of which is the point E', similar to the point B'.

It should be noted that the segments 50 and 55 cannot have points of intersection because of the possible displacement of the means for support 30 and of the object 45 as illustrated in FIG. 6. To overcome this disadvantage, the means for processing 100 translates the center T' of the support 30' in order to make it coincide with the center T of the means for support 30, the effect of which is to provide the configuration of FIG. 5, in which the axes 50 and 55 intersect at a point C. If segments of interest do not overlap or intersect with the others, they are then not considered in the calculation of the calibration, nor are the images associated with them: they are assumed to correspond to another object.

The calibration factor corresponds to a magnification factor or to any other equivalent factor. Thus, the relative position of the object with respect to the X-ray source is determined directly, hence, knowing the relative position of the X-ray source and of the means for acquisition due to its construction, the magnification factor of the image of the object, and therefore the calibration, are determined. The user of the method does not have to carry out any action in order to calculate the calibration of the image and the patient is subject only to X-ray radiation which is strictly needed for producing the image required for diagnosis.

An embodiment of the method and the device has at least one of the following additional features:

(a) acquiring an image of the object to be X-rayed;
(b) selecting a point, a segment or an area on this image;
(c) determining a corresponding projected segment or area or volume, this segment or area or volume comprising the region of interest whose center of gravity is determined; and
(d) the region of interest being defined as corresponding to the set of points which, between the means for support and the means for acquiring an image is projected onto the whole image.

In addition, the method comprises analyzing additional images of the object to be X-rayed acquired during the same examination, for which respective additional regions of interest in which the object is likely to be found are determined.

In addition, the method comprises:

(a) determining an intersection between the regions of interest thus defined for the various images;
(b) calculating the center of gravity of this intersection;
(c) determining the calibration factor of the images as a function of the position thus determined:
(d) the region or regions of interest are segments lying between the means for support and the means for acquiring an image; and
(e) a position of center of the means for support is translated, on acquiring additional images, to a position of a center of the means for support so as to cause them coincide, then the intersection of the segments of interest thus translated is determined.

According to an embodiment of the invention, a radiography device of the type comprises an X-ray source, means for acquiring an image placed facing the X-ray source, and means for support placed between the X-ray source and the means for acquiring an image, on which means for support an object to be X-rayed is intended to be positioned, is also provided, the device comprising means for processing at least one image acquired by implementing the method having at least one of the aforementioned features.

Various modifications in structure and/or steps and/or function may be made by one skilled in the art without departing from the scope and extent of the invention as recited in the claims.

What is claimed is:

1. A method of calibrating images acquired by a radiography device that comprises:

means for providing a radiation source;
means for acquiring images;
means for support placed between the means for providing a source and the means for acquiring images, on which support an object to be imaged is positioned between the means for support and the means for acquiring images, comprising:
analyzing images of the object to be imaged, for which respective regions of interest in which the object is likely to be found are determined;
determining an intersection between the regions of interest thus defined for the images;
calculating a center of gravity of this intersection; and
determining at least one calibration factor of the images as a function of the center thus determined.

2. The method according to claim 1 comprising:

acquiring an image of the object to be imaged;
selecting a point, a segment or an area on this image; and
determining a corresponding projected segment or area or volume, the segment or area or volume comprising the regions of interest in whose center of gravity is determined.

3. The method according to claim 2 wherein the regions of interest are segments lying between the means for support and the means for acquiring images.

4. The method according to claim 3 comprising:

on acquiring images, a position of a center of the means for support is translated to another position of a center of the means for support so as to cause the positions to coincide; and
determining an intersection of the segments of interest based on the translation.

5. The method according to claim 1 wherein the regions of interest are defined as corresponding to a whole volume which, between the means for support and the means for acquiring images, is projected onto a whole image.

6. The method according to claim 5 wherein the regions of interest are segments lying between the means for support and the means for acquiring images.

7. The method according to claim 6 comprising:

on acquiring images, a position of a center of the means for support is translated to another position of a center of the means for support so as to cause the positions to coincide; and
determining an intersection of the segments of interest based on the translation.

8. The method according to claim 1 wherein the regions of interest are segments lying between the means for support and the means for acquiring images.

9. The method according to claim 8 comprising:

on acquiring images, a position of a center of the means for support is translated to another position of a center of the means for support so as to cause the positions to coincide; and
determining an intersection of the segments of interest based on the translation.

10. A radiography apparatus comprising:

means for providing a radiation source;
means for acquiring images;
means for support placed between the means for providing a source and the means for acquiring images, on which support an object to be imaged is intended to be positioned;
means for processing at least one image acquired by the means for acquiring images;
means for analyzing images of the object to the imaged, for which respective regions of interest in which the object is likely to be found are determined;
means for determining an intersection between the regions of interest thus defined for the images;
means for calculating a center of gravity of this intersection; and
means for determining at least one calibration factor of the images as a function of the center thus determined.

11. The apparatus according to claim 10 wherein the regions of interest are defined as corresponding to a whole volume which, between the means for support and the means for acquiring images, is projected onto a whole image.

12. The apparatus according to claim 11 wherein the regions of interest are segments lying between the means for support and the means for acquiring images.

13. The apparatus according to claim 12 comprising:

means for translating a position of a center of the means for support to another position of a center of the means for support so as to cause the positions to coincide; and determining an intersection of the segments of interest based on the translation.

14. The apparatus according to claim 11 comprising:

means for translating a position of a center of the means for support to another position of a center of the means for support so as to cause the positions to coincide.

15. The apparatus according to claim 10 wherein the regions of interest are segments lying between the means for support and the means for acquiring images.

16. The apparatus according to claim 15 comprising:

means for translating a position of a center of the means for support to another position of a center of the means for support so as to cause the positions to coincide; and means for determining an intersection of the segments of interest based on the translation.

17. The apparatus according to claim 10 comprising:

means for translating a position of a canter of the means for support to another position of a center of the means for support so as to cause the positions to coincide.

* * * * *